United States Patent [19]
Miles

[11] Patent Number: 5,222,174
[45] Date of Patent: Jun. 22, 1993

[54] FIBER DIVERTER

[76] Inventor: Gregory M. Miles, 1925 McKinley Ave., Ste. D, La Verne, Calif. 91750

[21] Appl. No.: 659,636

[22] Filed: Feb. 25, 1991

[51] Int. Cl.⁵ ............................................. G02B 23/26
[52] U.S. Cl. .................................. 385/118; 385/117; 606/15; 606/16
[58] Field of Search ............... 350/96.10, 96.22, 96.24, 350/96.29, 96.32; 385/117, 125, 39, 78, 54, 118; 606/11, 14, 15, 16

[56] References Cited

U.S. PATENT DOCUMENTS

| | | | |
|---|---|---|---|
| 3,897,134 | 7/1975 | Scrivo et al. | 350/96.22 |
| 4,583,539 | 4/1986 | Karlin et al. | 350/96.32 X |
| 4,772,093 | 9/1988 | Abele et al. | 350/96.24 X |
| 4,778,247 | 10/1988 | Carpenter | 350/96.10 X |
| 4,988,163 | 1/1991 | Cohen et al. | 350/96.29 |

*Primary Examiner*—John D. Lee
*Assistant Examiner*—Phan T. Heartney
*Attorney, Agent, or Firm*—Michael R. Collins

[57] ABSTRACT

A device which incorporates three functions in one instrument necessary during surgical operations for transfer of laser energy to and viewing the site of the surgery. The fiber optic cable used to transfer the laser energy and the aspirator and irrigator tubes are all contained in a parallel in the fiber diverter. In addition the end of the fiber diverter can be bent at angles to the longitudinal axis of the instrument in order to work around other surgical apparatus involved in the operation thus avoiding the need to make other incisions in the patient. The amount of bend in the tip is controlled at the handle end of the instrument away from the surgical site. When bent the device can irrigate and aspirate at the same time laser cutting is being performed.

4 Claims, 2 Drawing Sheets

FIBER DIVERTER

FIELD OF THE INVENTION

The invention relates to devices for handling laser fiber optics, and, in particular to devices for using fiber optics in surgical operations. The new device incorporates fiber optic, irrigator and aspirator in a parallel configuration to allow application at the surgical site.

DESCRIPTION OF RELATED ART

Currently in use are laser fiber optic systems for cutting and other operations as well as fiber optics for viewing which position a fiber for use in surgery. In such instruments the optical fiber is contained in a channel so that the fiber can be safely brought to the required area. These instruments require separate aspiration and irrigation equipment to perform their functions. The current fiber optic devices are rigid instruments which do not allow for ease in application at the point of surgery when other instruments are being used as part of the surgery.

The present invention combines the laser fiber channel, the irrigator and the aspirator into one instrument. The three separate functions are contained in parallel channels to each other so that they may be employed at the same operation point. Another advantage of the new invention is directional control of the end of the device allowing 45 to 50 degrees of bend at the tip.

SUMMARY OF THE INVENTION

A primary objective of the present invention is to improve laser fiber optic handling devices for surgical and other uses by employing a parallel channel system of the fiber optic, aspirator and irrigator all in one compact instrument. This allows application of all three functions at the surgical site in an easy to handle and manipulate configuration for operating personnel.

A further object of the invention is to provide a means to apply the three functions at angles of bend up to 45 to 50 degrees. This is useful when the fiber optic device must be used under or around other surgical operation devices without interfering in the operation. Thus the surgeon can view the operating area via some microscope or camera system and the laser fiber optic can be used to operate in an unobstructed manner while other surgical tools are also in use at the operating site.

In accordance with the description presented herein other objects of this invention will become apparent when the description and drawings are reviewed.

DESCRIPTION OF THE PREFERRED EMBODIMENT

The fiber diverter consists of three parallel components, a laser fiber optic channel, an irrigation tube and an aspiration tube, contained in the same device. All three functions are required in surgery and the new invention puts them all in one instrument for efficiency of application at the site of operation. In addition the end of the device can be bent by twisting the bend control mechanism to allow application of the three functions in restricted spaces.

Figure 1:
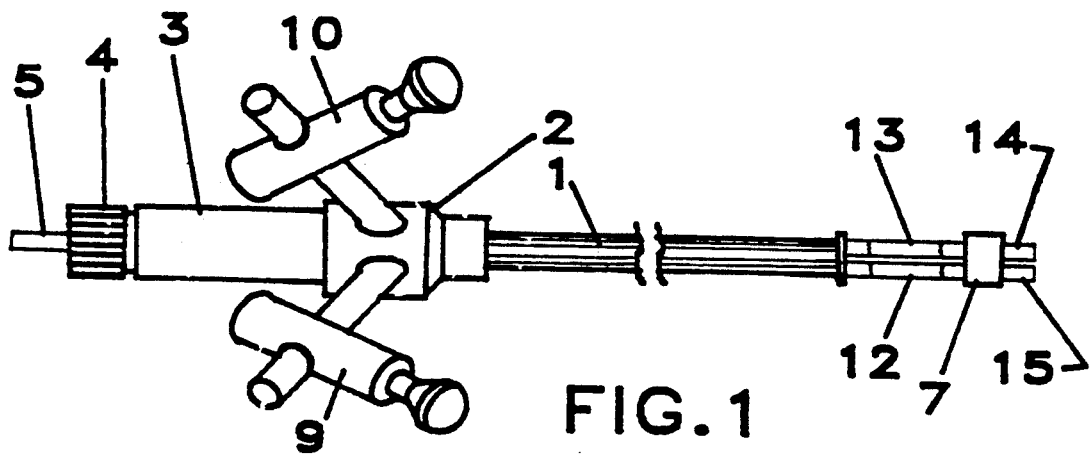
FIG. 1 illustrates a top view of the fiber diverter.
Figure 2:
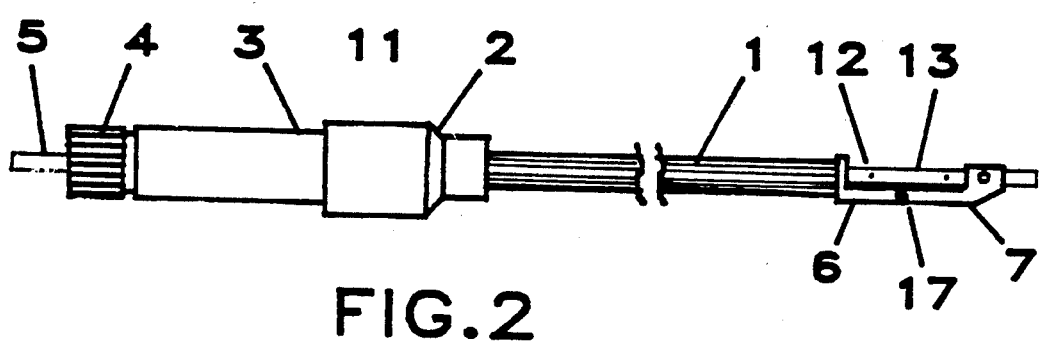
FIG. 2 illustrates a side view of the fiber diverter showing the aspirator side.
Figure 3:
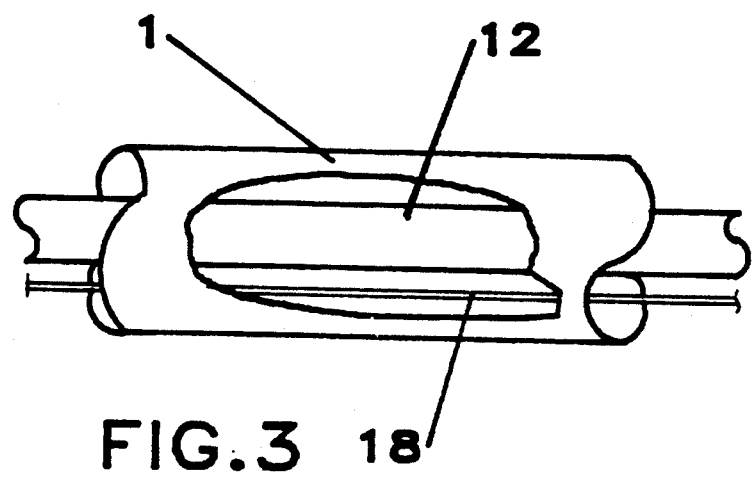
FIG. 3 illustrates a cut away view of the housing with a view of the tubes, wire and fiber optic cable.

Referring to FIGS. 1 through 3, the fiber diverter has a housing (1) attached to a valve distribution chamber (2) in a handle (3) having a feed control (4) and fiber optic feed (5) at its end. At the housing (1) end opposite the handle (3) there is a directional tip comprising a frame (6) and a guide hinge (7). All of these elements are longitudinally attached to provide a channel for a fiber optic cable, an aspiration function and an irrigation function.

A fiber optic cable from a laser device is fed into the fiber diverter through the handle (3) end via the optic feed (5). The cable passes through the feed control (4), handle (3), valve distribution chamber (2), and housing (1) to emerge at the frame (6) and pass through the guide hinge (7) via an aperture therein. The end of the fiber optic cable is then held in place by a retaining ring for application to the surgical site to perform surgery such as cutting with the laser.

The valve distribution chamber (2) has two apertures (11) to which an aspiration valve (9) and an irrigation valve (10) are attached at an angle to the longitudinal axis of the fiber diverter. Any standard type valve may be used for control such as a trumpet valve as shown in FIG. 1 or a stop cock valve. The aspiration valve (9) and irrigation valve (10) each connect to a tube (12) in the valve distribution chamber (2) which tube (12) continues through the housing (1) to emerge from the frame (6). The tube (12) protrudes from the frame (6) a sufficient distance, approximately ½ inch, to allow a sleeve (13) to be fit over it. The sleeve (13) is of a flexible material such as plastic, silicon or other similar type material to allow repeated bending.

Figures 5, 7, 8:
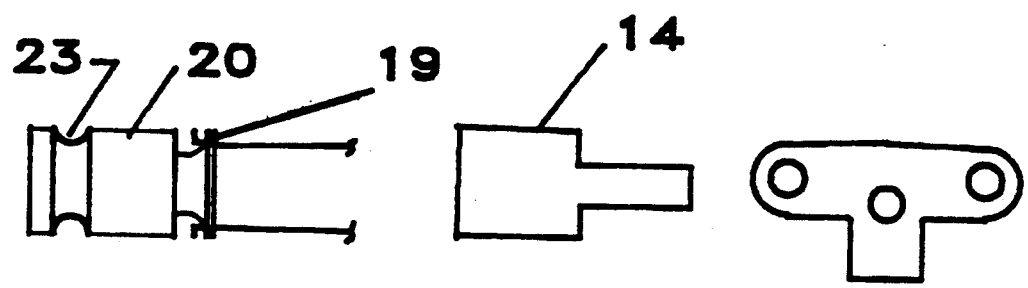
FIG. 5 illustrates the controller with wires.
FIG. 7 illustrates a tip.
FIG. 8 illustrates a front view of the guide hinge.

The guide hinge (7) is attached to the frame (6) to allow one degree freedom of movement at hinge point (17). The guide hinge (7) has three apertures, one for the fiber optic cable, one for the aspiration function and one for the irrigation function as shown in FIG. 8. The irrigation tip (14) and aspiration tip (15) are approximately one inch tubes with one half their length of slightly larger diameter than the other half as shown in FIG. 7. The smaller diameter end is of proper diameter to fit in the guide hinge (7) aperture. The larger diameter end prevents the tips (14) and (15) from passing through the aperture.

The irrigation tip (14) and aspiration tip (15) have the sleeves (13) fit over their larger diameter ends. When the directional tip is bent the sleeves (13) bend allowing the fiber diverter to be located at surgical operation points under or around other surgical operation equipment. the tips (14) and (15) are allowed to slide freely in the guide hinge (7) apertures yet are retained by their larger diameter end from being pushed out by the constant flexing of the sleeves (13).

Figure 6:
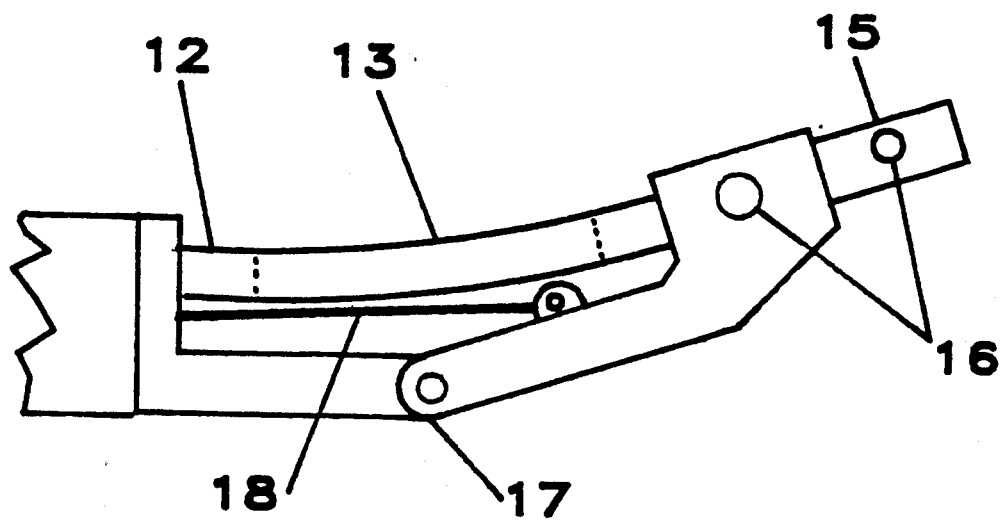
FIG. 6 illustrates a side view of the directional tip bent at an angle.

Referring to FIG. 6, the aspiration tip (15) has holes (16) on the side of the tube to prevent clogging and allow sufficient paths for removal of material from the surgical site. The tips (14) and (15) are normally metal, but can be of other suitable rigid material.

Figure 4:
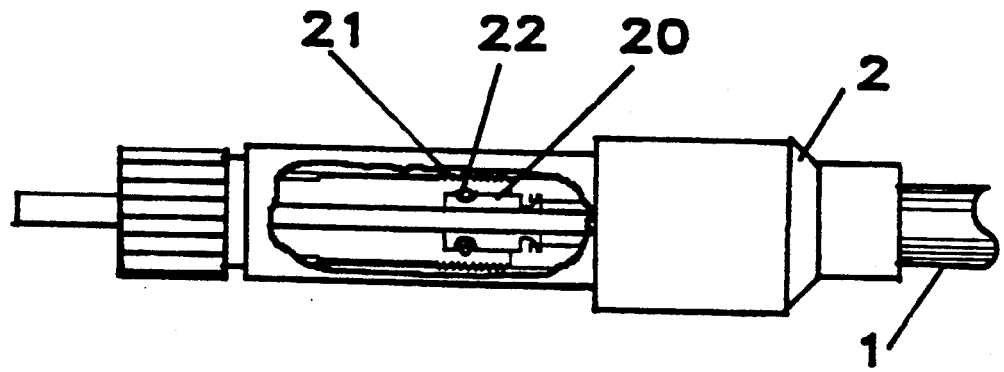
FIG. 4 illustrates a cut away view of the handle.

Referring to FIGS. 4 through 6 the directional tip is shown bent at an angle about the hinge point (17). The angle of the bend is controlled by wires (18) attached at one end to the guide hinge (7) and, after passing through the housing (1) and valve distribution chamber (2), attached at their other end to the wire holes (19) in controller (20). The controller (20) is retained in a control insert (21) by pins (22) holding the controller (20) in annular groove (23). The control insert (21) is threaded into a threaded aperture in handle (3). by twisting the feed control (4) relative to the handle (3) the controller (20) is moved longitudinally by a screw motion of the movement of the handle (3) threads relative to the control insert (21) threads. As the controller (20) moves with the control insert (21) the wires (18) are pulled or pushed relative to the housing (1) and frame (6) causing the guide hinge (7) to rotate about the hinge point (17).

The controller (20) has a longitudinal aperture through which the fiber optic cable passes as it traverses the handle (3).

I claim:

1. An apparatus for controlling and diverting a laser fiber optic cable, aspirator and irrigator comprising:
  a. a cylindrical housing attached to a valve distribution chamber at one end and a handle with a feed control and a fiber optic feed attached to the valve distribution chamber, and at the opposite end of the housing from the handle a directional tip is attached all of which elements as attached from a hollow center providing a longitudinal channel for passing a fiber optic cable, an aspiration tube and an irrigation tube in parallel;
  b. a frame and a guide hinge joined at a hinge point allowing one degree of freedom of bend movement wherein the guide hinge has apertures for the fiber optic cable, an irrigation tip and an aspiration tip;
  c. the irrigation tip and aspiration tip are approximately one inch tubes with one half their length of slightly larger diameter than the other half wherein the smaller diameter end is of proper diameter to fit in the guide hinge apertures and the larger diameter end will not pass through;
  d. a sleeve which is a flexible tube that fits over the larger diameter ends of the tips and the other end of the sleeves fit over the end of the aspiration tube and irrigation tube protruding approximately ½ inch from the frame;
  e. a wire attached to the guide hinge at a point which when the wire is pulled the guide hinge rotates about the hinge point relative to the frame and the wire passed through the housing, the valve distribution chamber and the handle to be attached to the end of a controller;
  f. the controller being retained in a control insert and allowed to rotate freely therein and the control insert having a threaded end opposite the controller end which threaded end is threaded into matching threads in the handle and a portion of the control insert protruding from the end of the handle being rigidly fixed to the feed control;
  g. an aspiration valve and an irrigation valve mounted in the valve distribution chamber having two apertures for such valves where the valves are attached to an angle to the longitudinal axis of the fiber diverter which is sufficient to allow use of the handle and not interfere with valve operation; and
  h. the aspiration valve and the irrigation valve are connected to the aspiration tube and the irrigation tube respectfully.

2. An apparatus for controlling and diverting a laser fiber optic cable, aspirator and irrigator comprising:
  a. a cylindrical housing attached to a valve distribution chamber at one end and a handle with a feed control and a fiber optic feed attached to the valve distribution chamber, and at the opposite end of the housing from the handle a directional tip is attached all of which elements as attached from a hollow center providing a longitudinal channel for passing a fiber optic cable, an aspiration tube and an irrigation tube in parallel;
  b. a means for control of the amount of flow through the aspiration tube and the irrigation tube;
  c. a frame and a guide hinge joined at a hinge point allowing one degree of freedom of bend movement wherein the guide hinge has apertures for the fiber optic cable, an irrigation tip and an aspiration tip;
  d. the irrigation tip and aspiration tip are approximately one inch tubes with one half their length of slightly larger diameter than the other half wherein the smaller diameter end is of proper diameter to fit in the guide hinge apertures and the larger diameter end will not pass through;
  e. a sleeve which is a flexible tube that fits over the larger diameter ends of the tips and the other end of the sleeves fit over the end of the aspiration tube and irrigation tube protruding approximately ½ inch from the frame;
  f. a wire attached to the guide image at a point which when the wire is pulled the guide hinge rotates about the hinge point relative to the frame and the wire passed through the housing, the valve distribution chamber and the handle to be attached to the end of a controller; and
  g. the controller being retained in a control insert and allowed to rotate freely therein and the control insert having a threaded end opposite the controller end which threaded end is threaded into matching threads in the handle and a portion of the control insert protruding from the end of the handle being rigidly fixed to the feed control.

3. The apparatus as in claim 2 or 1 wherein the sleeve is of a flexible material such as silicon plastic.

4. The apparatus as in claim 2 or 1 wherein the aspiration tip has holes on the sided of the smaller diameter portion.

* * * * *